United States Patent
Hattori et al.

(10) Patent No.: US 8,247,222 B2
(45) Date of Patent: Aug. 21, 2012

(54) MICRO-CHAMBER PROCESSING APPARATUS FOR CELL CULTURE AND METHOD

(75) Inventors: Akihiro Hattori, Tokyo (JP); Kenji Yasuda, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/036,600

(22) Filed: Feb. 28, 2011

(65) Prior Publication Data
US 2011/0212522 A1 Sep. 1, 2011

Related U.S. Application Data

(62) Division of application No. 10/544,799, filed as application No. PCT/JP2004/001941 on Feb. 19, 2004, now Pat. No. 8,008,069.

(30) Foreign Application Priority Data

Feb. 26, 2003 (JP) ................. 2003-048659

(51) Int. Cl.
  *C12M 1/00* (2006.01)
  *C12M 1/34* (2006.01)
(52) U.S. Cl. .............. 435/292.1; 435/289.1; 435/325
(58) Field of Classification Search .......... 435/289.1, 435/292.1, 325
See application file for complete search history.

(56) References Cited

U.S. PATENT DOCUMENTS

| | | | |
|---|---|---|---|
| 4,603,105 A | 7/1986 | Kaplan | |
| 7,846,717 B2 | 12/2010 | Yasuda et al. | |
| 2006/0141619 A1 | 6/2006 | Hattori et al. | |

FOREIGN PATENT DOCUMENTS

| | | |
|---|---|---|
| EP | 1344817 | 9/2003 |
| JP | 06-054899 | 3/1994 |
| JP | 08-172956 | 7/1996 |
| JP | 10-191961 | 7/1998 |
| JP | 11-169703 | 6/1999 |
| JP | 2002-153260 | 5/2002 |
| JP | 2002-245904 | 8/2002 |
| JP | 2003-135586 | 5/2003 |

OTHER PUBLICATIONS

Moriguchi et al., "An agar-microchamber cell-cultivation system: flexible change of microchamber shapes during cultivation of photo-thermal etching," Lab on a Chip. The Royal Society of Chemistry, May 2, 2002.

*Primary Examiner* — William H Beisner
*Assistant Examiner* — Michael Hobbs
(74) *Attorney, Agent, or Firm* — Jenkins, Wilson, Taylor & Hunt, P.A.

(57) ABSTRACT

This invention relates to a method and apparatus for processing cell cultures. The apparatus comprises a micro-chamber comprising no more than one absorption layer and at least one gel layer, in this order, laminated on a transparent base plate having no conspicuous absorbency in visible and infrared regions, and at least one light source, the absorption layer having absorbency in visible and infrared regions, and the gel-like material being a substance which has a gel dissolution temperature of 100 degree C. or less, solates when heated and is in a gel state at room temperature and has absorbency for a specific wave length of visible and infrared regions, and the light source having a monochromatic light in the specific wave length, wherein the light source is disposed such that it irradiates on the absorption layer and/or the gel layer, with the exception that when no absorption layer is provided, at least two layers each composed of a gel-like material are laminated on the transparent base plate.

4 Claims, 4 Drawing Sheets

(IRRADIATION TIME: 30s)

MICRO-CHAMBER PROCESSING APPARATUS FOR CELL CULTURE AND METHOD

CROSS REFERENCE TO RELATED APPLICATIONS

The present U.S. patent application is a divisional of U.S. patent application Ser. No. 10/544,799, filed Aug. 4, 2005, now U.S. Pat. No. 8,008,069, which claims the benefit of PCT International Application No. PCT/JP2004/001941, filed Feb. 19, 2004, which claims the benefit of Japanese Application No. 2003-048659, filed Feb. 26, 2003, the disclosures of each of which are incorporated herein by reference in their entireties.

FIELD OF THE INVENTION

The present invention relates to a micro-chamber processing apparatus and a micro-chamber processing method useful for the culture of cells.

PRIOR ART

Up to date, for the observation of a change in state of cells and a response to chemical agents, etc. of cells, it is common to observe the average value of some values of a cell population on the assumption that it is a property of one cell. However, actually, it is seldom that cells synchronize in their cell cycles in a group of them, but each cell rather develops a protein in a different cycle. In order to solve these problems, a technique such as a synchronous culture process, etc. has been developed. However, because cultured cells are not derived from one completely identical cell, there was a possibility that a difference in development of a protein is caused by a difference in gene of each cell derived before culture. Actually, when analyzing the results of responses to irritation, it was difficult to clarify whether its fluctuation derives from that of general responses possessed by a cell's reaction mechanism itself or whether it is derived from a difference in cell (that is, a difference in gene information). For the same reasons, with respect to cell lines it was difficult to clarify whether the reproducibility of responses to irritation fluctuates due to a difference in gene of each cell because it is generally not cultured from one completely identical cell. Further, from the fact that there are two types of irritation (signal) to cells, i.e., one being given by the amounts of signal substance, nutriment and dissolved gas contained in a solution in the circumference of a cell, and the other being provided by the physical contact between cells, it was the circumstance that it is difficult to judge its fluctuation.

On the other hand, heretofore, when cells are to be observed in a study field of biotechnology, it is common either to observe them by removing a portion of a cell group cultured in a large culture vessel and setting it on a microscope, or to conduct the observation with a microscope by enclosing the entire microscope with a plastic container to control the temperature and then placing another small container within the enclosure under the control of carbon dioxide concentration and humidity. Then, it is designed to exchange the used culture solution with a new culture solution while culturing cells whereby the solution conditions are maintained constant. For example, there are a process of maintaining nutrient conditions constant by means of a mechanism wherein a circulating pump operates upward and downward the level of a culture medium relative to the surface of a base material between a level higher than the upper end edge of the base material and a level lower than the lower end edge thereof in such a manner that when it decreases to the lower level, a culture medium is fed, while when it increases to the higher level, a culture medium is discharged (Japanese Patent Application Public Disclosure (Kokai) Hei 10-191961), and a process of maintaining the nutrient conditions of a culture vessel constant by inserting in a culture vessel one end of each of an inlet tube for introducing a new culture medium into the culture vessel, an outlet tube for discharging a culture medium from the culture vessel and a gas tube for communicating a gas portion of the culture vessel with a pump, wherein the inlet tube, the outlet tube and the gas tube are provided on their respective conduit line with a filter for preventing the intrusion of bacilli into the culture vessel (Japanese Patent Application Public Disclosure (Kokai) Hei 8-172956). However, in either of these inventions, a technique is not known wherein cells are cultured while controlling the solution environment of a cell to be cultured and the physical contact between cells.

Accordingly, we solved these problems, and invented a technique of selecting a specific new one cell only and culturing the one cell as a cell line, a technique wherein, when observing cells, the solution environment conditions of the cells are controlled and the cell concentration in the vessel is maintained constant, and a technique of observing the culture while specifying interacting cells (Patent Application Public Disclosure (Japanese Patent Application Public Disclosure (Kokai) 2002-153260). Further, we invented a micro-chamber for cell culture wherein the shape of a cell culture vessel can be freely varied while culturing cells in the region irradiated and heated with a convergent light (Patent Application No. 2002-245904).

Problems to be Solved by the Invention

In the preparation of micro-chambers for cell culture, it is possible to make electrode array base plates and physical barriers taking advantage of a micro-processing technique having been developed by utilizing a semi-conductor fabrication technique. In order to process and modify base plates, however, it was necessary to repeat complicated steps such as light exposure, etching, etc. in a clean room, etc. to previously incorporate therein a shape and a pattern prior to beginning of the culture of cells. Accordingly, it was difficult to simply alter the structure immediately before the commence of culture of cells, to process the shape during the culture of nerve cells, to alter the fine structure depending on the behavior of cells, and also to conduct the continuous processing while confirming the processing position with visual observation during processing.

By using, as a structural material for the base plate in the culture of nerve cells, a soft material (a gel-like material) which can be easily dissolved by heating with a convergent light, the present invention aims at providing a micro-chamber array technique by which it is possible to, simply and freely, add an etching process depending on the observation on the state of cells, and also it is possible to conduct the continuous processing while confirming the shape when processing, which were difficult in conventional micro-fabrication technique using, as the raw material, hard materials such as glasses, silicones, etc.

Means to Solve the Subject

We have now found that when a layer composed of a gel-like material having absorbency at a specific wave length of visible or infrared regions is formed on a base plate and this specific absorption wave length is then irradiated on the resulting layer with the use of a light source of a monochromatic light, preferably a laser, whereby a chamber of a desired shape is formed in the layer composed of a gel-like material, then the resulting chamber is very suitable for cell culture, and attained the present invention.

The micro-chambers formed according to the processing apparatus or method of the present invention have advantages that (1) the micro-processing is possible immediately before the commence of cell culture or during the culture of cells, (2) it is possible to control the expansion of a physical or biochemical neurite taking advantage of the inertness to cells and the non-adhesiveness to cells of a gel-like material such as agarose, etc., (3) the etching is possible with a resolution power of approximately 1 μm; It is easy to form a complicated shape such as a tunnel-type channel, etc., which was formed only according to a complicated process in prior arts, (4) micro-structures can be easily fabricated only with a convergent light-type heating apparatus without necessity of using expensive equipments such as a clean room, a mask aligner, a dry etching apparatus, etc., and like.

That is, the present invention is a micro-chamber processing apparatus for cell culture comprising a micro-chamber and at least one light source, wherein said micro-chamber comprises no more than one absorption layer and at least one gel layer composed of a gel-like material (hereinafter called "gel layer") or at least two gel layers when no absorption layer is provided, in this order, laminated on a transparent base plate having no conspicuous absorbency in visible and infrared regions, said absorption layer has absorbency in visible or infrared region, said gel-like material is in a gel state at room temperature, which has a gel dissolution temperature of 100 degree C. or less and solates when heated, said gel-like material has absorbency at a specific wave length of visible or infrared region, said light source has a monochromatic light at said specific wave length, and said light source is disposed such that it irradiates on said absorption layer and/or said gel layer.

Further, the present invention is a method for processing micro-chambers for cell culture which comprises the steps of:

preparing a micro-chamber comprises no more than one absorption layer and at least one gel layer composed of a gel-like material or at least two gel layers when no absorption layer is provided, in this order, laminated on a transparent base plate having no conspicuous absorbency in visible and infrared regions, said absorption layer has absorbency in visible or infrared region, said gel-like material is in a gel state at room temperature, which has a gel dissolution temperature of 100 degree C. or less and solates when heated, said gel-like material has absorbency at a specific wave length of visible or infrared region, and irradiating at least one visible or infrared monochromatic light on the absorption layer or the gel layer composed in the micro-chamber to form therein a gel-free region of a desired shape.

Further, the present invention is a method for culturing cell which comprises, in addition to the method as in above, a step of injecting a cell and its culture solution into a formed region free from a gel substance.

EMBODIMENTS OF THE INVENTION

Figure 1:
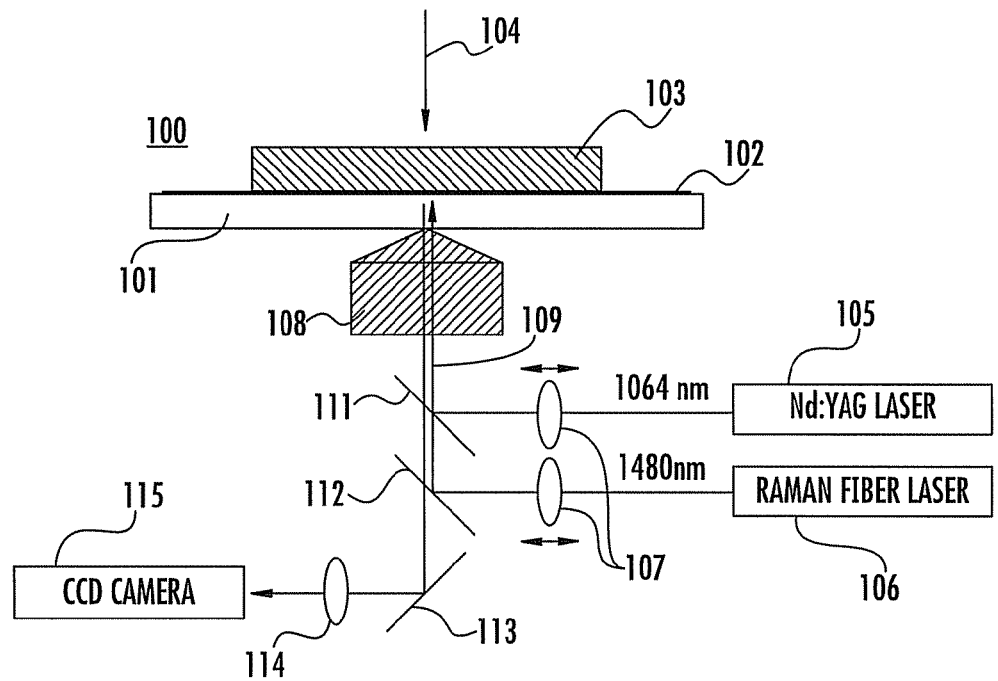
FIG. 1 shows one embodiment of a micro-chamber processing apparatus according to the present invention, wherein reference numerals indicate those parts as follows; 100: a micro-chamber for cell culture, 101: a base plate, 102: an absorption layer, 103: a gel layer, 104: a visible light for optical observation, 105, 106: a light source of a specific wave length, 107, 114: an optical lens, 108: an objective lens, 109: a convergent light of a specific wave length, 111,112: a mirror refracting a light of a specific wave length, 113: a mirror, and 115: a camera for observation.

First, we will describe the constitution of a micro-chamber according to the present invention.

It is desirable that the transparent base plate is a material which has no conspicuous absorbency in visible and infrared regions and is optically transparent for the light of a wave length selected for processing. It is preferable that this base plate has a relatively small absorption of less 0.1% as compared with that of the absorption layer as described hereinafter for all wave lengths of visible and infrared regions used in the processing apparatus of the present invention. More particularly, it is possible to use glasses such as borosilicate glass, quartz glass, etc., plastics such as polystyrene, etc., solid base plates such as a silicone base plate, etc. and high molecular materials such as agarose, etc.

On this base plate is disposed an absorption layer having absorbency in visible and infrared regions. It is preferable that this absorption layer is a film formed of Cr or a metal oxide such as aluminum oxide, etc. In general, these films have an even absorption over the entire wave length of visible and infrared regions. However, there are absorption and scattering peaks depending on the wave length of a light and the film thickness such as Fabry-Perot. It, therefore, is better that it is thinner than the wave length of a light used. It is preferable that it has an absorption of 1,000 times or more that of a light of a layer containing a gel-like material as described hereinafter for the wave length used. For example, for a wave length of 1064 nm, the deposited Cr layer of 5 nm has an absorption of 10% or more relative to irradiated light. The absorption of agarose is 0.01% or less. This absorption layer can be also omitted.

Further, the base plate per se or the base plate having an absorption layer thereon can be treated with a collagen molecule or polylysine. The surface per se of the glass base plate can be made water-penetrative by oxygen ashing. For example, the surface of an absorption layer such as a deposited layer of chromium, etc. can be subjected to a silane-making treatment, on which is applied and fixed a cell absorption element such as collagen, etc. Then, the processing can be conducted so that the cells can be stably adhered on the bottom of a hole. The conditions of such surface treatments can be determined according to necessity depending on a cell to be cultured and its object.

On this absorption layer is disposed at least one gel layer having absorbency for a specific wave length of visible and infrared regions, which material is a substance which has a gel dissolution temperature of 100 degree C. or less preferably 45 degree C. or less, solates when heated and is in a gel state at room temperature. The micro-chamber of the present invention features using a plurality of layers including an absorption layer. Therefore, when it has no absorption layer, at least two layers each composed of a gel-like material are laminated on the base plate.

This gel-like material is a substance which undergoes a change in phase of from a sol into a gel or from a gel into a sol in its solution when heated or cooled, wherein this sol-gel change can irreversibly take place at a specific temperature of from 0 to 100 degree C. This substance assumes a molecular structure of the random coil type in its heated solution. When this solution is cooled, a portion of the substance assumes a helical structure so that it produces a network. As a result, it is believed that this substance loses finally its fluidity so that it gels. When continuously cooled, this gel network increases with time so that it forms a stronger gel.

Such substances include straight chain polymers obtained by the purification of biogenic materials such as, for example, collagen, agarose, agaropectin, galactose, anhydrogalactose, galacturonic acid and its methyl ester, etc. However, it is also possible to use synthetic high molecules having the above functions. Particularly, it is believed that it is optimum to use agarose because it has no adhesiveness to cells and is not signal substance against cells so that it is nontoxic to cells, and thus has little affection on culture test data.

This substance is dissolved in water or a buffer, etc. in a concentration of generally from 0.2 to 10% depending on use applications whereby a gel-like material is formed.

This gel-like material can be a combination of gel-like materials having each a different gel dissolution temperature. For example, although they are different depending on the chain length, etc. of purified molecules, in general, collagen has a gelation temperature of from 15 to 20 degree C. and a gel dissolution temperature of 20 to 30 degree C., and agarose and agaropectin have each a gelation temperature of from 30 to 40 degree C. and a gel dissolution temperature of 85 degree C., respectively. For galactose and anhydrogalactose, the gelation temperature is from 30 to 75 degree C. and the gel dissolution temperature is from 5 to 10 degree C. higher than the gelation initiation temperature. For galacturonic acid and its methyl ester, the gelation temperature is from 60 to 80 degree C. and the gel dissolution temperature is from 60 to 80 degree C. under the conditions of a sugar level of 65 degree or more and a pH of 3.5, and the gelation temperature is from 30 to 40 degree C. and the gel dissolution temperature is from 30 to 40 degree C. in the presence of a calcium ion.

Further, a substance (dye, etc.) absorbing infrared lights or visible lights can be incorporated in this gel-like material so that it has absorbency for a specific wave length.

This gel-like material has an Abs of generally less than 0.01 for an optical path length of 1 cm with respect to a wave length for which it has no absorbency.

The thickness of the layer of this gel-like material can be determined at need according to its object. In general, it is on the order of from 100 nm to 2 nm.

When this gel-like material is used in the form of a multi-layer structure, the layers each composed of a gel-like material may have each a different absorption wave length, and also may have each a different dissolution temperature. Further, these layers may be laminated in such a manner that the gel dissolution temperature gradually increases toward above on a base plate.

The micro-chamber of the present invention may either one which has one absorption layer and one gel layer laminated on a base plate, or one which has two layers each composed of a gel-like material laminated on a base plate and has no absorption layer thereon. Three or more materials having each a different melting point can be also laminated thereon. Further, the micro-chamber can be three-dimensionally divided into some zones so that it has a region of a different melting point and a region of a different absorbency. It is possible to stepwise select a dissolution region by controlling the type and strength of a heated and focused light. More particularly, it can be realized by laminating thereon low melting agaroses having each a different melting point. However, it is also possible to use different materials such as agarose, plastics, etc.

The light source used in the processing apparatus of the present invention emits a monochromatic light in visible and infrared regions. The light source can be used singly or in a combination of two or more. It is preferable that the light source is a laser. These lasers include Nd:YAG laser (1064 nm), Raman Fiber laser (1480 nm), titanium sapphire laser (variable in 500-1100 nm), Alexandrite laser (variable in 700-818 nm), color center laser (variable in 800-4,000 nm), OPO laser (variable in 400-800 nm), etc.

Such light sources are disposed in such a manner that they irradiate on an absorption layer and/or a gel layer. Particularly, it is preferable that they are disposed such that they can focus and irradiate a light on either of an absorption layer and/or a gel layer.

Further, this light source can be composed of two or more light sources having each a different wave length, at least one wave length of which may be an absorption wave length for either gel layer. Alternatively, it can consist of one light source, the wave length of which may be an absorption wave length for either gel layer.

The processing apparatus may further have an instrument means, preferably, an optical microscope, for confirming the position of a light radiated from a light source during irradiation. By the disposition of such an instrument means, the processing shape or processing stage can be visually confirmed optically with the use of a weak observation light.

In the processing apparatus having the above constitution, a monochromatic light is irradiated on an absorption layer or a gel layer. When it is irradiated on an absorption layer, a portion of a gel layer is locally dissolved by the heat generated in the absorption layer. On the other hand, when a light of an absorption wave length for a gel-like material is irradiated on this gel-like material, the gel-like material is locally dissolved so that the material itself diffuses into the layer. Then, the resulting space is filled with a water or buffer contained in the gel layer. By moving the position of such a light irradiation according to necessity, a water- or buffer-filled space of a desired shape can be formed within a gel layer. The shape of such a space is not particularly restricted to any form, but a cylindrical or rectangular body having a hole of from 2 μm to 1 mm in diameter, a passageway having a diameter of 2 μm to 1 mm and a length of from 2 μm to 1 mm, and the like can be formed.

In such a manner, a desired shape can be formed in a gel layer. An outward opened hole can be formed in an inner space, or a pipe can be inserted from outside into an inner space, whereby a cell or its culture solution is injected into or discharged from its space.

Further, the gel layer can be covered over its outer surface with an optically transparent semipermeable membrane such as cellulose, etc. whereby the contamination with extraneous microbes, etc. is prevented and also it is possible to prevent cells from escaping out from the hole. Then, for example, when the gel layer is agarose and the semipermeable membrane is cellulose, a portion each of sugar chains of the both is ring-opened so as to modify avidin and biotin which have each an amino end in the —CHO residue whereby the semipermeable membrane can be bonded to the gel layer through an avidin-biotin bond. When it is necessary to cycle a culture solution in the culture of cells, a gel layer is covered with an optically transparent container of a shape covering over the entire layer. Thus, a culture solution can be introduced into the container through a tube, and a waste liquid of the culture solution can be recovered from another tube communicating with the container.

Now, we will describe an embodiment each of a micro-chamber processing apparatus, a processing method and a micro-chamber formed thereby according to the present invention. The present invention is not to be restricted to the following embodiments so that various embodiments are possible.

FIG. 1 shows one embodiment of the micro-chamber processing apparatuses of the present invention. In a micro-chamber for cell culture 100 according to the present invention, an absorption layer (a film layer) 102 having optical absorbency such as a deposited layer of chromium, etc. is disposed on an optically transparent base plate 101 such as a slide glass, etc. For the observation with a transmitted light, it is desirable that the absorption layer 102 has a film thickness of the order that it does not entirely absorb a light and that it is uniformly thin. For example, when the absorption layer is a chromium deposit, it has a film thickness of 50 Å wherein the transmitted light is approximately 70% in a visible region. Then, on the absorption layer 102 is laminated a layer 103 composed of a gel-like material such as agarose, etc., which is optically transparent, has a low melting point and is free of toxicity to cells, etc. In the layer 103 are then formed a plurality of holes for the introduction of a sample such as cells, etc. according to a process described hereinafter. Thus, a specific cell can be cultured in their respective hole.

The apparatus of FIG. 1 has a means for irradiating two or more convergent lights each of a different wave length through an objective lens on a layer 103 composed of a gel-like material to thereby process the shape of the layer 103. More particularly, for example, with respect to the light irradiated from a light source 105 which generates a monochromatic light of 1064 nm having no absorbency for water, the position of a focal point at which it passes through an objective lens 108 can be controlled by adjusting the position of a lens 107. The position of this focal point can be adjusted by the visual confirmation by means of an optical microscopic instrument means. Further, with respect to the light irradiated from a light source 106 which generates a monochromatic light of 1480 nm having absorbency for water, the position of a focal point within a micro-chamber can be likewise controlled by adjusting the position of the lens 107. These monochromatic lights can be introduced into the optical paths of the objective lens by means of mirrors 111 and 112, respectively.

Further, in the apparatus of the present invention, the image observed by a visible light source 104 can be focused on the light-receiving surface of a camera 115 by means of a lens 114 in order to confirm a position to be processed by a convergent light of the specific wave length.

Figure 2:
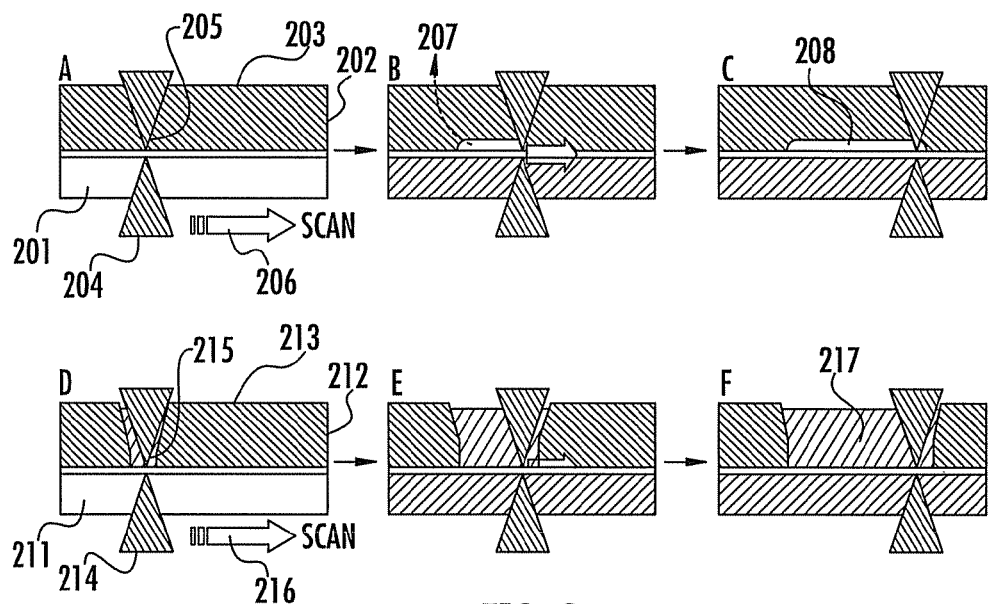
FIG. 2 illustrates a step of processing a desired shape in a micro-chamber. Reference alphabets a through c indicate a procedure of forming a tunnel, and d through f indicate a procedure of forming an upward opened hole, wherein reference numerals 204, 214: a convergent light, 205, 215: a focal point of a convergent light, 206,216: a movement direction of a convergent light, 207: a diffusion direction of a solated material, 208: a tunnel, and 217: a hole.

FIG. 2 shows a step of processing, by the combination of two convergent lights each of a different wave length, a desired shape in a micro-chamber comprising one absorption layer and thereon one layer (for example, 200 μm in thickness) composed of a gel-like material disposed on a base plate.

FIG. 2 a to c show a procedure of forming a tunnel 208 by irradiating a convergent light of, for example, 1064 nm on an absorption layer. First, a convergent light 204 of 1064 nm is absorbed in an absorption layer 202 absorbing a light of this wave length in the vicinity of a focal point 205 so that the resulting heat dissolves a portion of a layer 203 composed of a gel-like material. This gel-like material itself diffuses into the layer 203, and instead the space thus formed is filled with a water or buffer contained in the layer 203. Then, when the position of this focal point 205 is moved to a direction of the arrow 206 (FIG. 2 b), a tunnel 208 filled with water or a buffer is formed, with the movement of the focal point, in the layer 203 composed of a gel-like material as shown in FIG. 2 c.

As shown in FIG. 2 d to f, when a monochromatic convergent light 214 of 1480 nm is irradiated on a layer 213 composed of a gel-like material, with respect to a layer 213 composed of a water-containing material such as agarose, etc. all of the material are heated and dissolved on an optical path 214 as water absorbs a convergent light of 1480 nm. As a result, an upward opened hole is formed in the layer 213 composed of a gel-like material (FIG. 2 d). A cell or its culture solution can be injected or discharged through such an upward opened hole. Further, as shown in FIG. 2, when this focal point 215 is moved to a direction of the arrow 216, the shape of the tunnel is thereby enlarged (FIG. 2 f).

Figure 3:
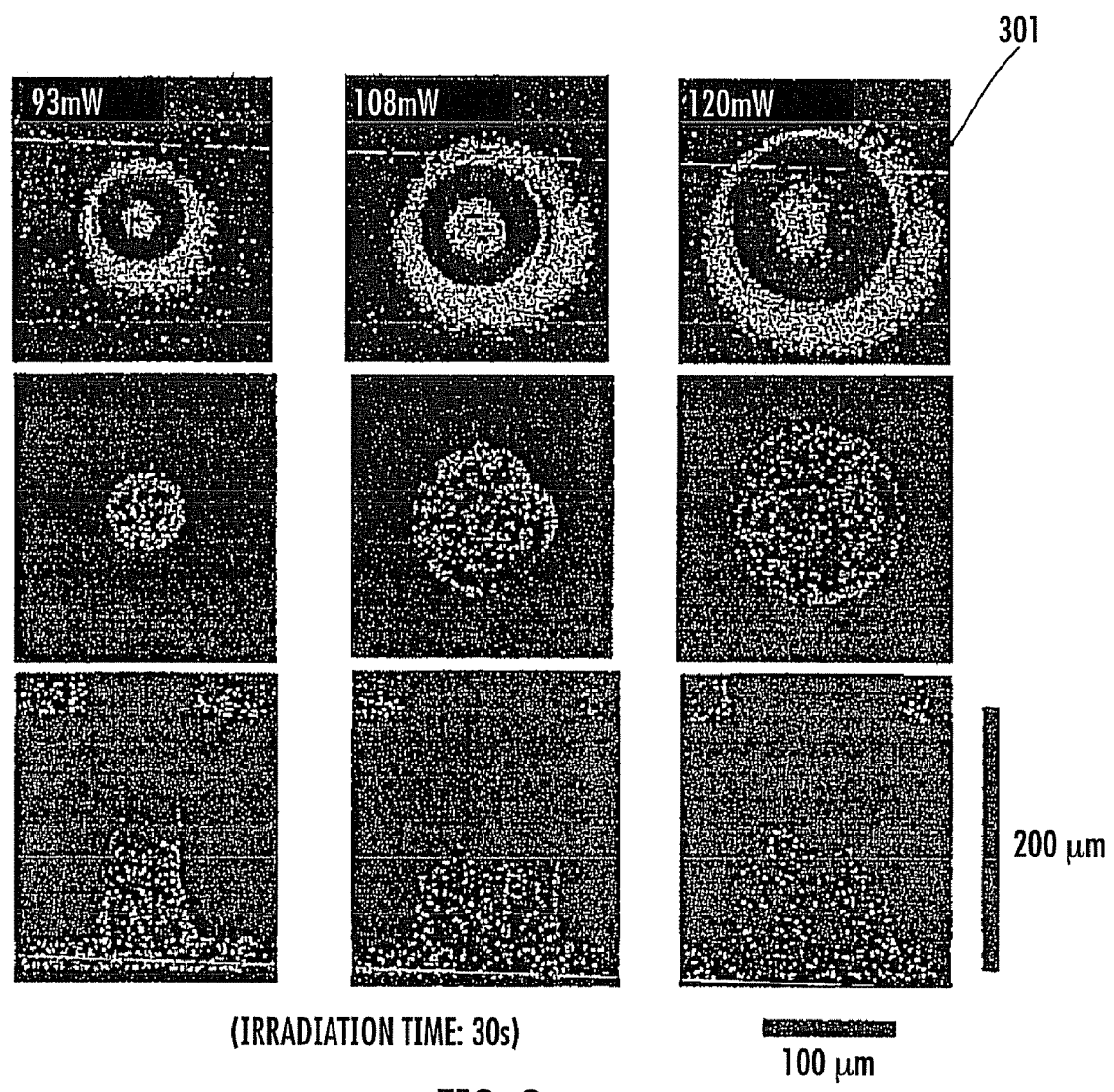
FIG. 3 shows microphotographs illustrating one embodiment of a micro-chamber processing method. Rows show the results of different laser strengths (93 mW, 108 mW, 120 mW), wherein the upper rows show phase-contrast microscopic images, the middle rows show top surface images obtained by a confocal scanning microscope, and the lower rows show cross section images obtained by a confocal scanning microscope, wherein reference numeral 301 indicates a hole.

FIG. 3 shows microphotographs of the holes thus formed. FIG. 3 illustrates a case where holes are formed by irradiating a convergent light of 1480 nm for 30 seconds on a base plate having agarose coated thereon. From this figure, it can be confirmed that holes are formed along the optical path in an agarose layer of 200 μm in thickness.

Figure 4:
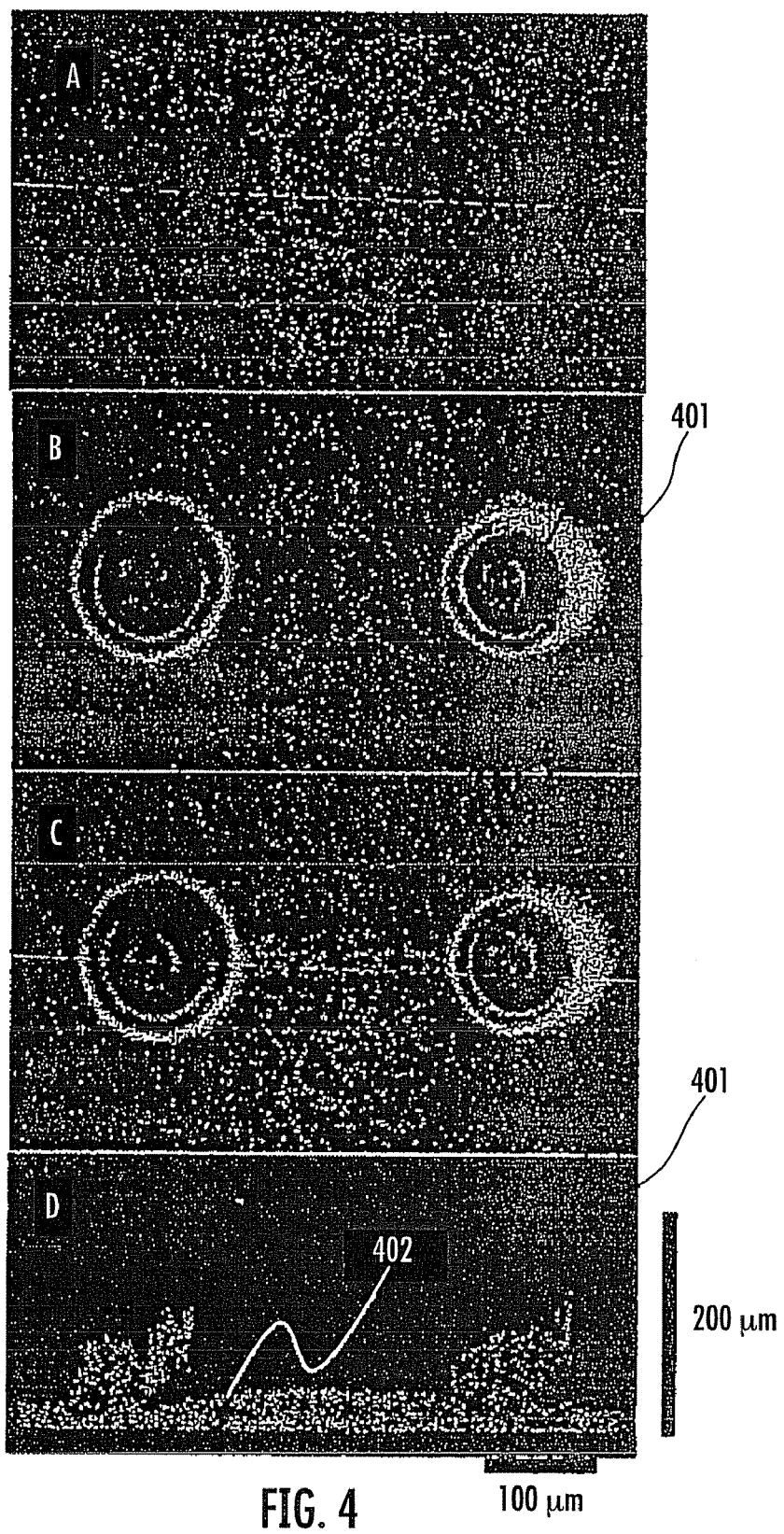
FIG. 4 shows microphotographs illustrating one embodiment of a micro-chamber processing method. Reference alphabets a through c are microphotographs as seen from the top surface, and d is a confocal scanning microscopic image showing the cross section of a base plate at stage c, wherein reference numerals 401 and 402 indicate a hole and a tunnel, respectively.

FIG. 4 shows one example of processing procedures using two irradiation lights each of a different wave length. For example, by stepwise using a monochromatic light of 1064 nm and a monochromatic light of 1480 nm, holes as well as a tunnel for connecting these holes can be formed. FIG. 4 a shows a photograph of a base plate before the irradiation of a light, and FIG. 4 b shows holes 401 formed with a monochromatic laser light of 1480 nm according to the procedure illustrated in FIG. 3. After two holes are formed, as shown in FIG. 4 c and d the absorption layer is irradiated with a wave length of 1064 nm for which agarose has no absorbency (according to the same procedure as that of FIG. 2 a-c) to form a tunnel 402 on the bottom of an agarose layer whereby two holes can be connected to each other.

Figure 5:
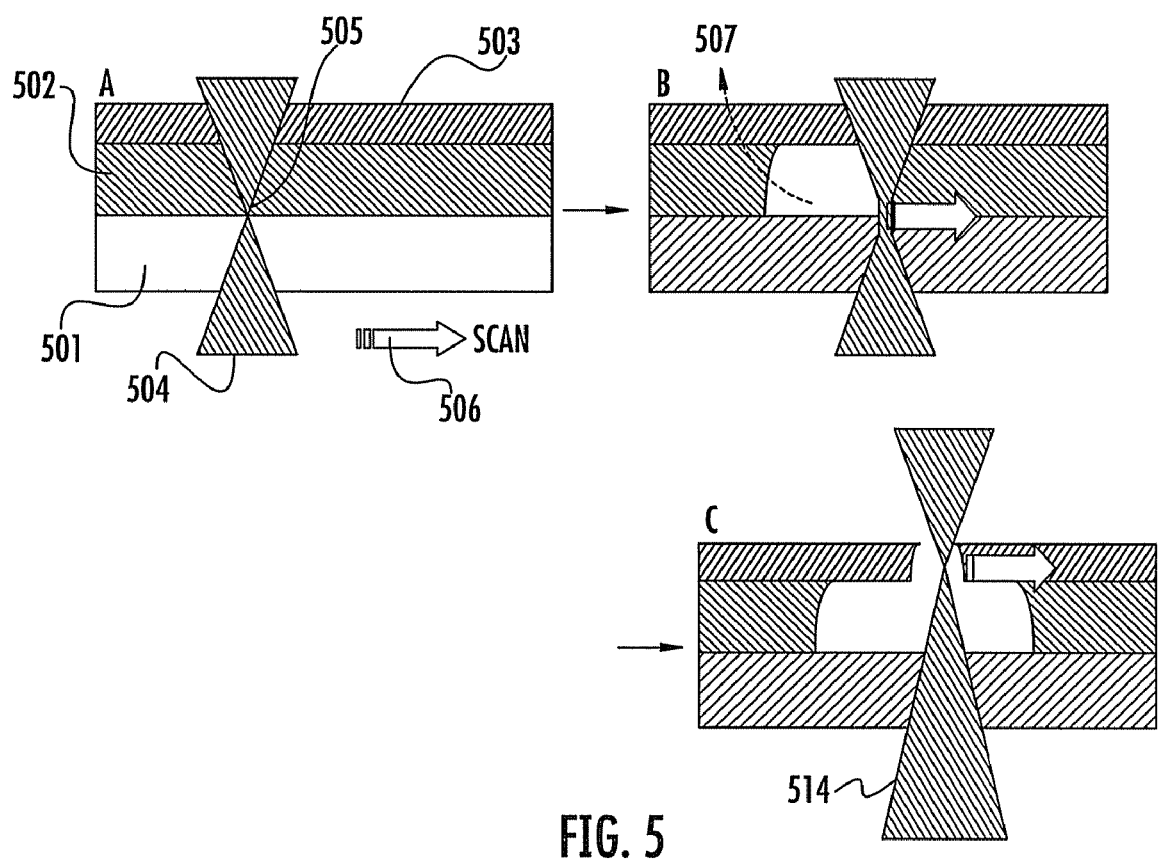
FIG. 5 shows microphotographs illustrating one embodiment of a micro-chamber processing method, wherein reference numerals indicate those parts as follows; 501: a base plate, 502, 503: a gel layer having a different absorption wave length or gel dissolution temperature, 504, 514: a convergent light, 505: a focal point of the convergent light, 506: a movement direction of the convergent light, and 507: a diffusion direction of a solated material.

FIG. 5 shows a process of forming a complicated shape by laminating on a base plate 501 two layers 502 and 503 each composed of a gal-like material having a different absorption wave length and then using two convergent lights 504 and 514 to selectively dissolve a layer 502 only and a layer 503 only, respectively. First, a wave length absorbed in the layer 502 only is used as shown in FIG. 5 a, and the layer 502 only is processed as shown in FIG. 5 b. Second, as shown in FIG. 5 c, the layer 503 is processed with the use of a wave length absorbed in the layer 503. Thus, it is possible to process complicated shapes.

It is also possible to form similar shapes by laminating on a base plate 501 two layers 502 (low gel dissolution temperature) and 503 (high gel dissolution temperature) which are each composed of a gel-like material having a different gel dissolution temperature, and varying its irradiation time with the use of a light source of one wave length.

Advantages of the Invention

As discussed in detail, according to the present invention it is possible to vary the shape of a culture vessel in response to a culture process while culturing bio-cells, etc., which was considered impossible up to date. Further, it is possible to form a structure by using a combination of a plurality of lights each having a different wave length to locally dissolve a substance in a region less than that of a light.

What is claimed is:

1. A method for processing a micro-chamber for cell culture, wherein the micro-chamber comprises at least two gel layers, the method comprising the steps of:

providing a transparent base plate having no conspicuous absorbency in visible and infrared regions;

providing at least two different gel materials which have different absorption wavelengths or different dissolution temperatures, or providing a gel material and adding a substance absorbing infrared or visible lights to at least a part of the gel material to thereby produce at least two different gel materials which have different absorption wavelengths or different dissolution temperatures, wherein the gel materials are in a gel state at room temperature, have a gel dissolution temperature of 100 degree C. or less, solate when heated, and have absorbency at a specific wave length of visible or infrared region;

laminating the at least two different gel materials on the base plate to form at least two gel layers; and irradiating at least one visible or infrared monochromatic light on at least one of the gel layers to form therein a gel-free region of a desired shape.

2. The method as in claim 1 wherein a monochromatic light is focused and irradiated on a first gel layer and a second monochromatic light is focused and irradiated on a second gel layer, to thereby form therein a gel-free region of a desired shape.

3. A method for culturing a cell which comprises, in addition to the method as in claim 1, a step of injecting a cell and its culture solution into a formed region free from a gel material.

4. A method for culturing a cell which comprises, in addition to the method as in claim 2, a step of injecting a cell and its culture solution into a formed region free from a gel material.

* * * * *